United States Patent [19]

Ragner

[11] Patent Number: 5,092,851
[45] Date of Patent: Mar. 3, 1992

[54] SAFETY NEEDLE WITH SPRING-LOADED SHIELD

[75] Inventor: Gary D. Ragner, Gainesville, Fla.

[73] Assignee: Ragner & Staab Associates, Gainesville, Fla.

[21] Appl. No.: 640,942

[22] Filed: Jan. 4, 1991

[51] Int. Cl.⁵ .............................................. A61M 5/32
[52] U.S. Cl. ...................................... 604/192; 604/263
[58] Field of Search ............... 604/192, 187, 198, 263, 604/110

[56] References Cited

U.S. PATENT DOCUMENTS

| | | | |
|---|---|---|---|
| 3,329,146 | 7/1967 | Waldman, Jr. | 604/192 |
| 4,863,435 | 9/1989 | Sturman et al. | 604/198 |
| 4,863,436 | 9/1988 | Glick | 604/198 |

FOREIGN PATENT DOCUMENTS 3808688  1/1989  Fed. Rep. of Germany ...... 604/198

*Primary Examiner*—John D. Yasko

[57] ABSTRACT

A device for protecting practitioners from inadvertent punctures with contaminated needles. The device comprises a safety shield (40), needle (51), handle (34), and a helical spring (35). Needle (40) and spring (35) are molded into handle (34) with needle tip (52) projecting forward. The opposite end of spring (35) is attached to shield (40) such that spring (35) is compressed when shield (40) is in a retracted position. Handle (34) comprises a receiving hub (28) with lock tabs (30) for securing the invention to a syringe, and a latching tube (37) with notches (38a and 38b) formed on the interior. The safety mechanism is activated by squeezing finger grips (36a) and (36b). This action increases the distance between notches (38a) and (38b), thereby releasing safety shield (40). Spring (35) is designed so that its natural length is slightly shorter than is necessary for center hole (48) to reach needle tip (52). However, the momentum of shield (40) carries it well past the natural length of spring (35) and causes shield (40) to extend past tip (52). The interior of shield (40) is designed with a cavity (44) which catches tip (52) as shield (40) returns toward handle (34). Because shield (40) can extend a considerable distance beyond needle (51) when released, the ensuing impact of shield (40) against tip (52) causes the blunting of tip (52) so that needle (51) can not be reused.

7 Claims, 5 Drawing Sheets

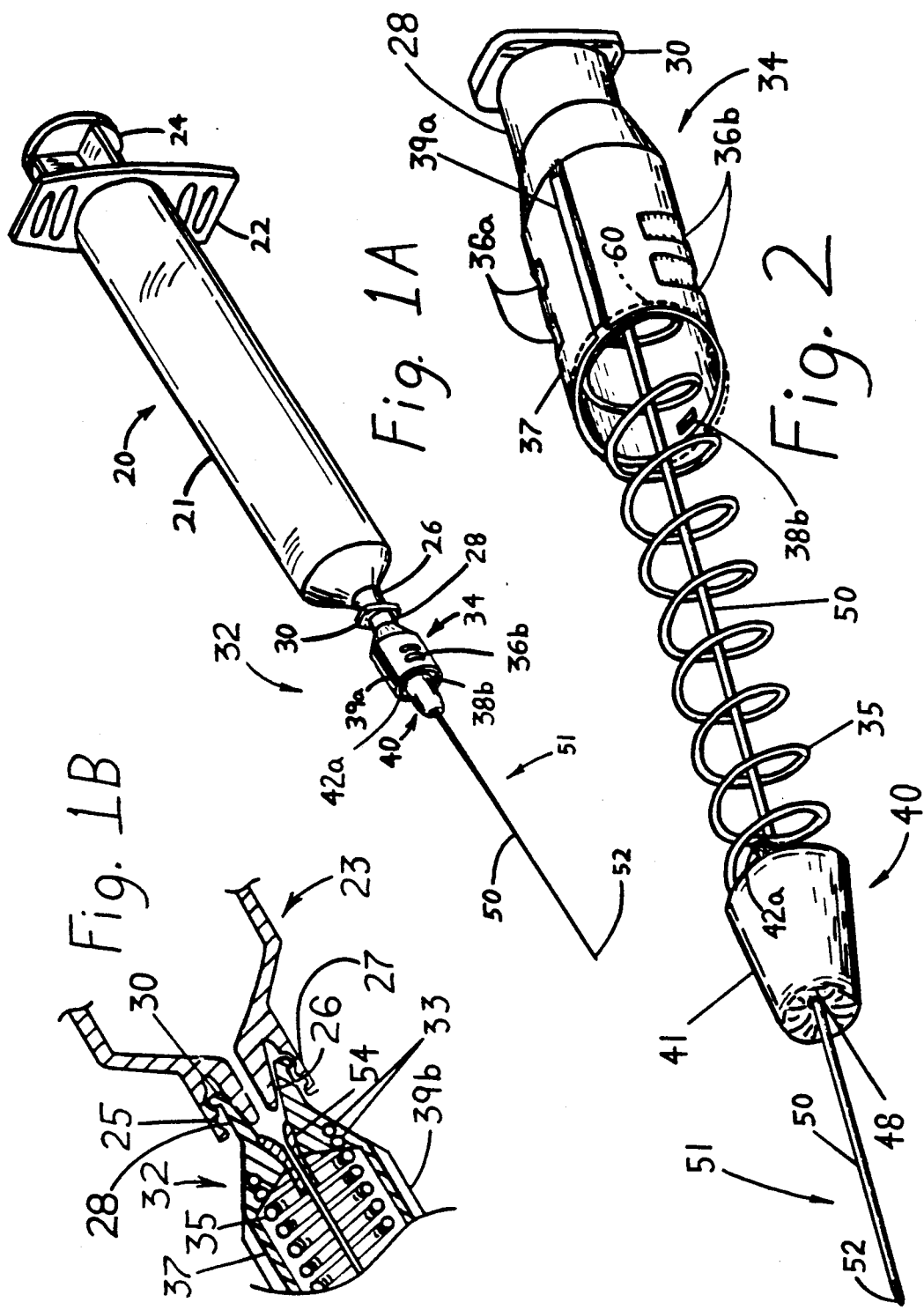

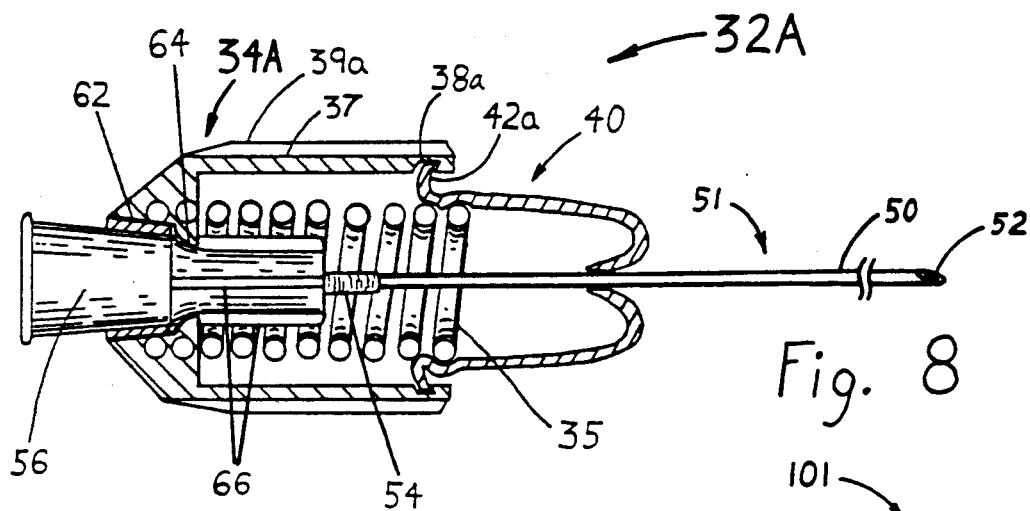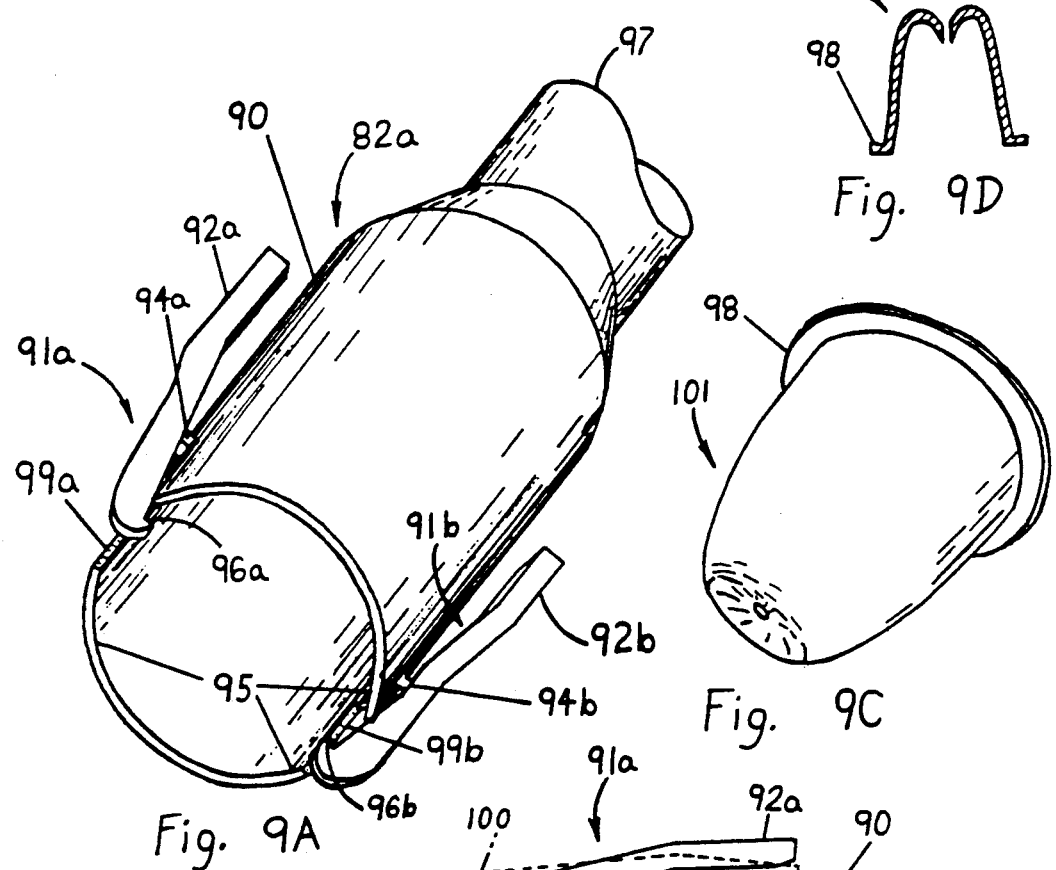

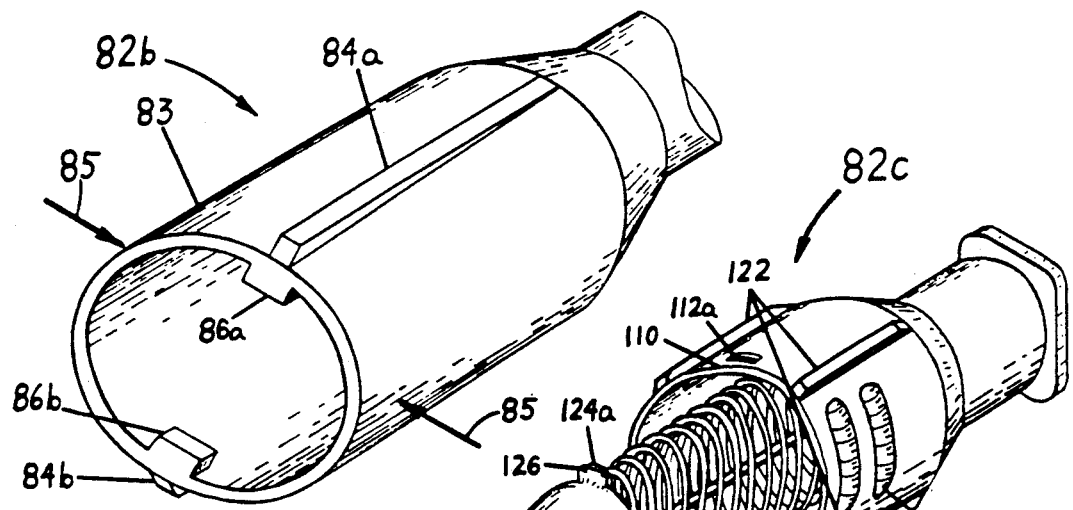
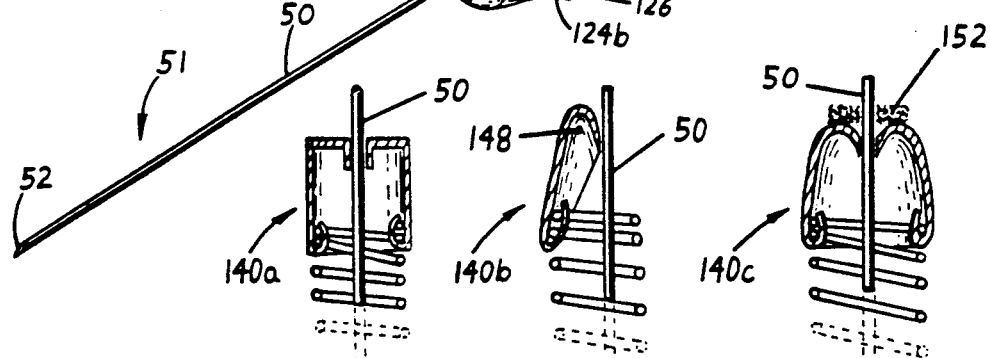
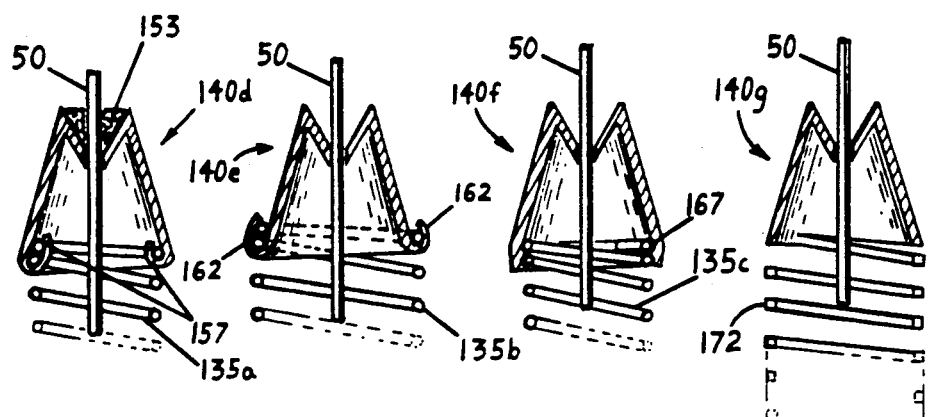

SAFETY NEEDLE WITH SPRING-LOADED SHIELD

BACKGROUND-FIELD OF INVENTION

This invention relates to medical needles and more specifically to protective means for preventing accidental sticks with contaminated needles.

BACKGROUND-DESCRIPTION OF PRIOR ART

Since AIDS appeared in 1981 there has been great effort to protect people from accidentally being stuck with a contaminated needle. In hospitals, millions of needles are used daily. Some of these needles are used on patients with blood transmitted diseases, and these needles can cause illness if someone is accidentally stuck.

Practitioners are at greatest risk of being stuck because of their exposure to contaminated needles. On average a doctor or nurse uses 20 to 30 needles per day. Many of these needles are thrown away several minutes after use. Reasons for not immediately throwing needles away include: caring for emergency patients, drop boxes are not near by, multiple injections being given, laziness, and forgetfulness. To counter this problem many people have designed safety devices which allow the user to immediately cover the sharp tip of the needle after use.

Of these safety devices a few have the shielding mechanism built into the needle's base. It is to this category that my invention pertains.

At present, needles come enclosed in sterile packaging; two protective caps, one covering each end of the needle. To use the needle one twists off the rear protective cap exposing the injection port of the needle. This is then pressed or twisted onto a syringe. Once in place the front cap is snapped off exposing the needle's tip. To keep this procedure from being hindered the shielding mechanism must be very compact. U.S. Pat. No. 4,911,706 to Levitt on Oct. 14, 1988, is a simple folding spring with a cap on the end which traps the needle's tip. The system is very simple but its sideways protruding spring would make attachment to a syringe difficult without contamination. Also, the system would be awkward when giving an injection.

A more compact design, U.S. Pat. No. 4,664,654 to Strauss on Mar. 7, 1986, uses a helical spring instead of a folding spring. In addition, Strauss has designed a locking system. Unfortunately, the shielding mechanism more than doubles the length of the system over a standard needle. U.S. Pat. No. 4,894,055 to Sudnak on Dec. 28, 1988, is a similar design using a helical spring with only a slightly more compact locking system.

U.S. Pat. No. 4,863,436 to Glick on Oct. 11, 1988, is a compact design but is useful only for very short needles. It also has another flaw in that the user must reach very near the tip of the needle to extend the protective cover; it would be better to have no cover at all.

My invention provides a simpler and more compact covering mechanism than the prior art. The user can activate the cover with a single hand and the sharp tip of the needle is destroyed in the process. My invention has the added advantage of being compatible with standard syringes and adds insignificantly to the size of a standard needle.

OBJECTIVES AND ADVANTAGES

Accordingly, several objects and advantages of my invention are:

(a) to provide a spring loaded safety shielding system that automatically covers the tip of the needle when the release means is pressed;

(b) to provide a compact safety shielding system which can be used with both hollow and solid-core needles;

(c) to provide a shielding system for needles of all lengths;

(d) to provide a shielding system which is easily incorporated into existing medical practices;

(e) to provide a shielding system which will fit easily into a sterile protective cap similar to those presently used with needles;

(f) to provide a compact shielding system which does not sufficiently increase the length of the needle;

(g) to provide a shielding system which covers the sharp tip of the needle, and also blunts the tip by dynamic impact;

(h) to allow the helical spring used in this invention to serve four separate functions: (1) extension means, (2) stopping means, (3) guiding means for the safety shield, and (4) the locking means for the safety shield;

(i) to provide a simple single piece latching system;

(j) to provide simple and easily operated latching system for release of the safety shield;

(k) to provide a shielding system that makes a distinctive click when the needle tip is protected properly.

(l) to provide a superior latching system that is not accidently released by pressure exerted on the needle, jarring of the system, or undirected force onto the release mechanism; and (m) to provide a simple to manufacture spring-loaded shield which consists of only two more parts than a standard needle (a standard needle consists of the needle shaft with a metal flange fitted on the rear portion of the needle and a molded plastic handle which is used to attach the needle to a syringe). To construct my invention the handle is reshaped to provide both an attachment mechanism and also a latching mechanism. The two added parts consist of a helical spring which is molded into the handle and a small safety shield which attaches to the spring. The shield is held in its cocked position by the latching portion of the handle.

A further advantage would be to prevent illegal drug users from re-using needles. Dynamic contact between the needle tip and the safety shield blunts the tip so that the needle can not be reused. This is unique because it damages the one thing a junky needs to inject drugs; that is, a sharp needle tip. Physically breaking the needle at the base, as is done in many hospitals, does not stop the use of that needle. Simply attaching the broken needle to an eyedropper makes the needle usable again. This method also makes use-once syringes no more effective at stopping drug abuse than normal syringes.

DRAWING FIGURES

FIG. 1A shows an isometric view of the invention attached to a syringe.

FIG. 1B shows a section view of invention attached to a syringe.

FIG. 2 shows an isometric view of the preferred embodiment of the invention.

Figure 5:
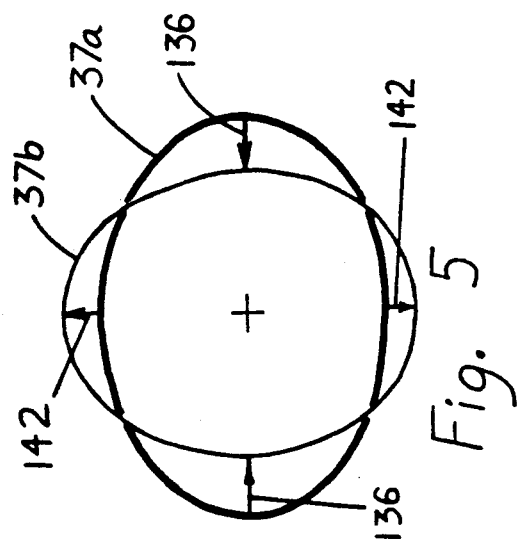

FIG. 5 a representative diagram of latching system and how safety shield is released.

Figure 6:
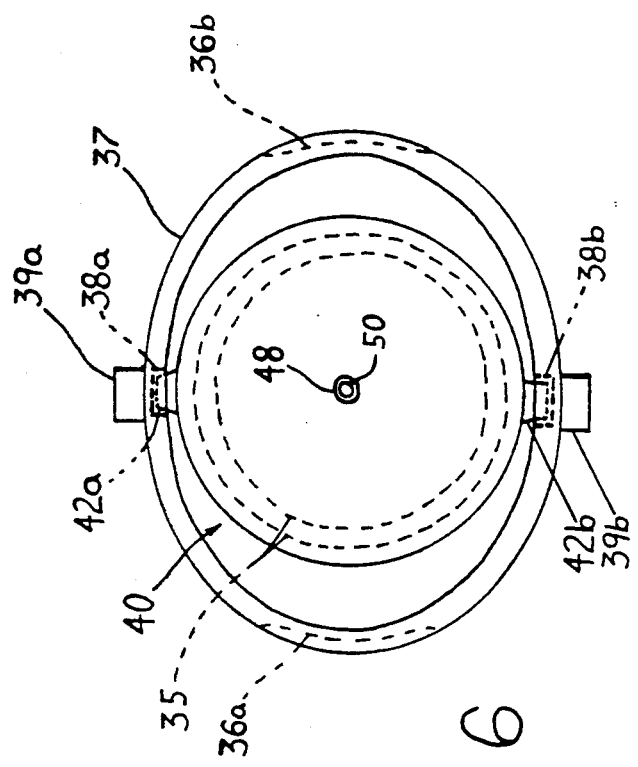

FIG. 6 shows an end view of safety needle.

Figure 7:
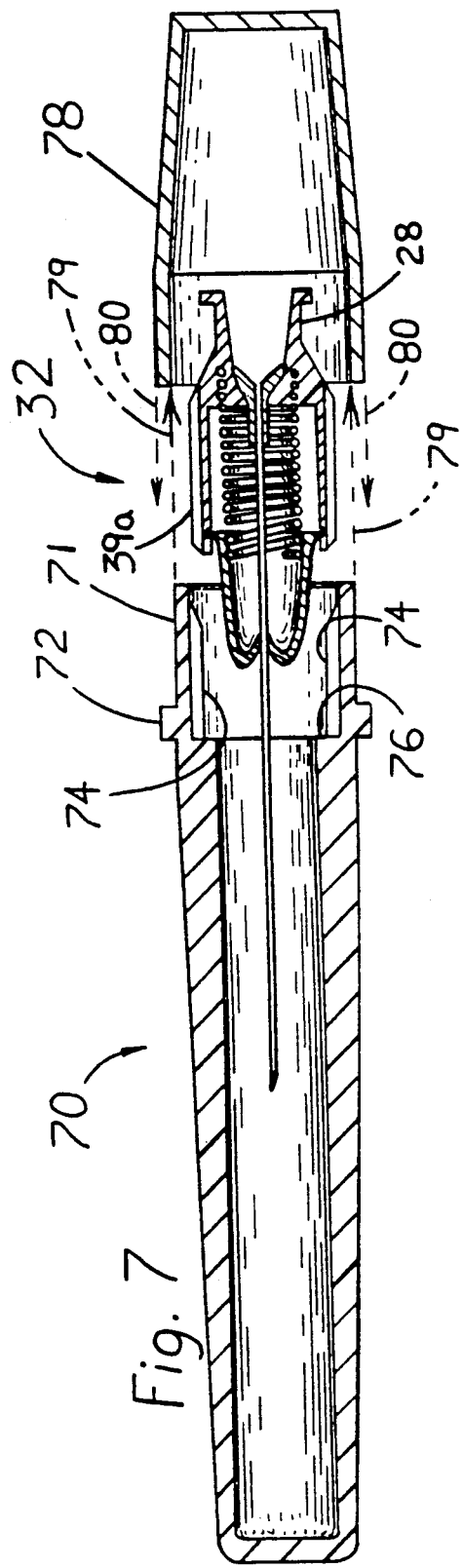

FIG. 7 shows a section view of the preferred embodiment of invention with protective caps.

FIG. 8 shows a section view of invention in the form of a attachment to standard needles.

FIG. 9A Shows a modified latch system where rocker arms are used to retain the safety shield.

FIG. 9B shows a section view of rocker arm latch system in FIG. 9a.

FIG. 9C Shows an isometric view of safety shield for latch systems shown in FIG. 9A and 9B.

FIG. 9D shows a section view of safety shield in FIG. 9C.

FIG. 10 shows a modified latch system where tabs on the latch tube retain the safety shield.

FIG. 11 shows a modified latch system where the latch notches go completely through the latch tube.

FIG. 12A-13A shows 4 different shapes for the safety shield.

FIG. 13A-13D shows 4 different means for attaching the spring to the safety shield.

DRAWING REFERENCE NUMBERS

| | | | |
|---|---|---|---|
| 20 | syringe | 74 | twist ridges |
| 21 | syringe barrel | 76 | latch tube stop |
| 22 | syringe finger grips | 78 | aft protective cap |
| 23 | modified syringe | 79 | slide motion of 70 |
| 24 | syringe plunger | 80 | slide motion of 78 |
| 25 | locking threads | 82a-c | modified latch assembly |
| 26 | syringe nozzle | 83 | tube section of 82b |
| 27 | syringe thread hub | 84a-b | twist ridges |
| 28 | receiving hub | 85 | release force |
| 30 | lock tabs | 86a-b | latch tabs |
| 32 | invention - preferred | 90 | tube section of 82a |
| 32A | modified safety needle | 91a-b | rocker arm |
| 33 | portion of spring in 34 | 92a-b | rocker arm handles |
| 34 | needle handle - 28,30,36a-b,38a-b, 39a-b | 94a-b | rocker arm pivots |
| | | 96a-b | catch on arms 91a-b |
| 34A | modified needle handle | 97 | hub 28 or interface 62 attaches here |
| 35 | helical spring | | |
| 36a-b | finger grips on handle 34 | 98 | beveled ridge |
| 37 | latch tube portion of 34 | 99a-b | gaps in 90 |
| 38a-b | latch notch of handle 34 | 100 | released position of 91 |
| 39a-b | ridge on handle 34 | 101 | modified safety shield |
| 40 | safety shield assembly - 41,42a-b,44,48 | 110 | tube section of 82c |
| | | 112a-b | latch slot |
| 41 | safety shield body | 114a-b | finger grips |
| 42 | latch flange of 40 | 120 | oval-shaped spring |
| 44 | concave recession in 40 | 122 | twist ridges |
| 46 | spot weld | 124a-b | latch flange |
| 48 | center hole in end of 40 | 126 | flange stop |
| 50 | needle shaft | 130 | modified safety shield |
| 51 | needle assembly - 50,52,54 | 135a-c | helical springs |
| | | 136 | motion of finger grips |
| 52 | needle tip | 140a-g | modified safety shields |
| 52a | needle tip after impact | 142 | motion of notches |
| 54 | needle base | 148 | cavity of shield 140b |
| 56 | needle hub | 152 | absorbent pad for 140c |
| 60 | circular reference | 153 | absorbent pad for 140d |
| 62 | attachment interface | 157 | inward crimp tabs |
| 64 | lock ring | 162 | outward crimp tabs |
| 66 | hub ridges | 167 | spot weld |
| 70 | front protective cap | 172 | spring cut from cap |
| 71 | attachment tube | | |

-continued
DRAWING REFERENCE NUMBERS

| | |
|---|---|
| 72 | stop ring |

DETAILED DESCRIPTION OF THE PREFERRED EMBODIMENTS

The most preferred embodiment of the safety needle is presented in FIG. 1A to FIG. 7. FIG. 1A shows the invention attached to a syringe 20. Syringe 20 consists of a nozzle 26 for communicating fluid into a needle, a syringe barrel 21 to hold the fluid, a plunger 24 to actuate the fluid, and a pair of finger grips 22 to aid gripping. Mounted on nozzle 26 of syringe 20 is the preferred embodiment of a spring-loaded safety needle 32.

Safety needle 32 comprising of four members; a medical needle 51 a molded plastic needle handle 34, a helical spring 35, and a safety shield 40. Needle 51 is of a standard design and consists of a sharp tip 52, a needle shaft 50, and a needle base 54. Handle 34 comprises a receiving hub 28, lock taps 30, finger grips 36a and 36b, a latch tube 37, latch notches 38a and 38b, twist ridges 39a and 39b. Shield 40 is a thimble shaped cap that comprises; a body 41, a pair of latch flanges 42a-42b, a center hole 48 and a concavity 44. Shield 40 is held in place by flanges 42a and 42b. Flange 42a is located opposite flange 42b on shield 40. Flanges 42a and 42b communicate with latching notches 38a and 38b to hold shield 40 in a retracted position. Notches 38a and 38b are located on the front portion of handle 34 which I call a latch tube 37. On tube 37 a pair of grips 36a and 36b are molded into the plastic. This gripping surface can consist of a simple texture pattern or troughs as shown in FIG. 1. The texture pattern can be molded into the plastic or small particles can be embedded into the plastic to provide the gripping surface. At the rear of handle 34, two small lock tabs 30 are molded onto hub 28.

FIG. 1B shows a section view of a second type of syringe 23 mated to the invention. The only difference between the syringe discussed in FIG. 1 and this second type of syringe is the addition of a set of locking threads 25. Threads 25 are molded on the inside of a circular hub 27 so that the threads 25 face nozzle 26. Lock tabs 30 communicate with threads 25 such that hub 28 fits securely over nozzle 26. Also in FIG. 1B the section of spring 35 which is molded into the handle is denoted by part number 33.

FIG. 2 shows the preferred embodiment of the invention with shield 40 positioned so spring 35 is in an unstretched condition. Spring 35 having an unstreched length such that hole 48 does not extend past tip 52 of shaft 50. Notches 38a and 38b (notch 38a on inside of tube 37 opposite notch 38b) extend partially into tube 37. Flanges 42a and 42b fit into notches 38a and 38b; securing shield 40 to handle 34. Ridges 39a and 39b are molded on opposite sides of tube 37. The ridges are of sufficient height to provide communication between ridges 74 (see FIG. 7) and ridges 39a and 39b. Tube 37 is oblong with ridges 39a and 39b positioned in the narrow direction such that the outside circumference shown by a dashed line 60 is circular. A pair of grips 36a and 36b are also molded into the outside of tube 37. The rear portion of handle 34 consists of hub 28 and lock tabs 30.

Figure 4:
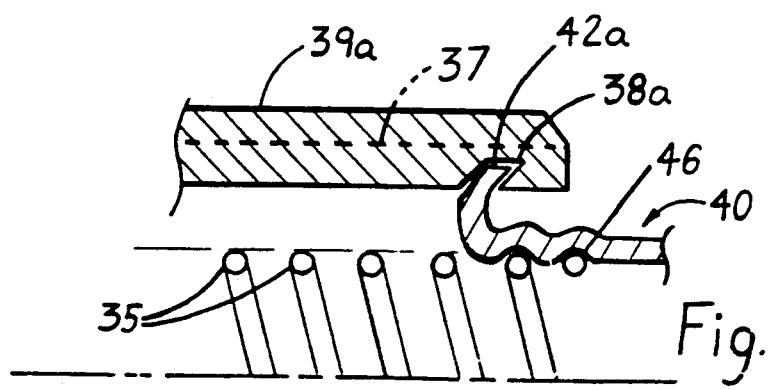
FIG. 4 shows a section view of latching system.

FIG. 4 shows a detailed section view of the latch system on one side of the invention. Flange 42a is beveled as is notch 38a which receives it. The bevel is used to reduce the risk of accidental release of the system.

FIG. 4 also details the attachment of spring 35 to shield 40. The spring is compression fitted into shield 40 with a spot weld 46 to keep the two pieces from slipping.

FIG. 6 shows an end view of the invention. Latch tube 37 is oblong, bulging out at the grips 36a and 36b. Shield 40 is released when one or both finger grips are pressed. The oblong shape allows the walls of tube 37 to be pressed inward without contacting either spring 35 nor shield 40. The oblong shape of tube 37 is not necessary, but does reduce the size of the invention. A round latch tube must have a larger volume to allow space for compression of the tube walls.

FIG. 7 shows a section view of the preferred embodiment of the invention with its two protective caps. A front cap 70 has a long hollow cavity which surrounds the needle. The aft portion of cap 70 consists of an attachment tube 71. Tube 71 receives safety needle 32 with the inside of 71 fitting snugly against tube 37. Twist ridges 74 on the inside of 71 communicate with ridges 39a and 39b providing transfer of twisting motion from cap 70 to safety needle 32. Cap 70 slides over safety needle 32 as shown by dashed arrow 79. Cap 70 is limited by a ring shaped stop 76 which contacts the front of tube 37 when completely installed. An aft protective cap 78 slides over tube 71 as shown by dashed arrow 80 and is limited by stop 72. The entire system is sealed together by melting a small portion of cap 78 onto stop 72. This effectively holds the two caps together but allows cap 78 to be easily broken off for use of safety needle 32.

FIG. 8 shows a section view of a spring-loaded safety needle attachment 32A. A standard needle consisting of; needle 51 (needle shaft 50, tip 52 needle base 54) and needle hub 56 with needle hub ridges 66, is inserted into the bore of safety attachment 32A. An attachment interface 62 connects hub 56 to an attachment handle 34A. 56 and 34A can be connected in several ways using cements, epoxies, shaping the contact surfaces to provide a locking snap fit, melting the two parts together and similar connective methods.

On the inside handle 34A is a locking ring 64; this ring serves to prevent shearing of interface 62. The ring has four notches which receive ridges 66. The communication between 64 and 66 stabilize the safety shield from twisting motions when ridges 66 is twisted on a syringe. If interface 62 consists of melting parts 56 and 34A the bond will have sufficient strength that ring 64 can be eliminated. The remaining portion of the safety shield is identical to the shielding system in FIG. 2. The system is also operated in the same manner. The remainder of the attachment is identical to the safety needle shown in FIGS. 1 to 7. The latch tube, spring, and safety shield are identical to those shown in FIGS. 1 to 7, and are identified with the same part numbers.

FIG. 9A shows an isometric view of second embodiment of the invention's latch tube assembly. Latch tube 90 is similar to tube 37 in FIGS. 1 to 8, however the latching system which is mounted on tube 90 is quite different from those previously shown. Latch tube assembly 82a would most preferably be injection molded as a single part but could be constructed with rocker arms 91a and 91b attached later. Where the aft end of 82a is cut, line 97, any number of attachments could be adapted to mount handle 82a to almost any medical instrument. One adaption would be to mold a receiving hub and twist lock tabs onto assembly 82a much like receiving hub 28 and lock tabs 30 are attached to handle 34 in FIG. 2. Pivots 94a and 94b attach arm 91a and 91b to tube 90. These flanges provide a pivot point by which the pivot arms can rotate about. Pivots 94a and 94b act as hinges for the pivot arms but still allow the system to be constructed from a single molded piece of plastic.

Catches 96a and 96b are molded into the ends of arms 91a and 91b respectively. These catches are opposite each other on tube 90. Catches 96a and 96b protrude through gaps 99a and 99b molded into tube 90. Catches 96a and 96b communicate with lip 98 on a safety shield 101 shown in FIG. 9C. Lip 98 is preferrably beveled to hold shield 101 more securely in its retracted position. Shield 101 has the same basic design as shield 40 and is shown in section in FIG. 9D. The difference between shield 40 and shield 101 is lip 98 replaces latch flanges 42a and 42b as a catch mechanism.

In FIG. 9B the top rocker arm is shown in a side view with tube 90 and shield 101 in section. Notice that when handle 92a is pressed, arm 91a moves to position 100. At position 100 catch 96a is lifted above the inner wall of tube 90 and shield 101 is released from assembly 82a. It should be noted that this design can be made to release shield 101 only when both rocker arms have been pressed or when a single arm has been pressed; this will be discussed in the operation section.

FIG. 10 shows an isometric view of a third embodiment of a latch assembly 82b. In this design latch tabs 86a and 86b are molded on the inside of a latch tube 83. As in assembly 82a, assembly 82b is used in conjunction with shield 101. Lip 98 holds shield 101 in its retracted position. In this design, tube 83 is flattened at tabs 86a and 86b. Twist ridges 84a and 84b are placed on the outside of tube 83 on these flattened sections. The ridges serve three functions: 1, to give tube 83 a circular cross-section to fit snuggly in a circular cap; 2, to provide a means of transferring twisting motion from a protective cap (similar to cap 70, FIG. 7) to tube 83; 3, to provide contact between inner walls of a protective cap keeping tabs from accidently moving apart and release its safety shield during shipping.

A fourth embodiment of a latching assembly is shown in FIG. 11. Latching assembly 82c is shown attached to a complete safety needle with its safety shield having just been released. In this design a latch tube 110 has a circular bore with 2 or more ridges 122. Ridges 122 serve to provide a means of transferring twisting motion from a protective cap to assembly 82c. The latching system uses two flanges 124a and 124b that fit into slots 112a and 112b which catch on to hold a shield 130 in its retracted position. To stop shield 130 from sliding around in slots 112a and 112b a flange stop 126 is placed below flanges 124a and 124b. These stops rest against the inside of tube 110 and thus holds shield 130 stable within the system.

When shield 130 is in its retracted position an oval shaped helical spring 120 is compressed. In this design spring 120 is not circular but has an oblong shape when looking down the axis of the spring. This oblong shape serves the purpose of allowing space for the inside walls of tube 110 to be pressed together where a set of finger grips 114a (opposite 114b) and 114b are located. This room is needed so that spring 120 does not interact with the walls of tube 110. If interaction occurs, shield 130 could be slowed sufficiently that it would not clear the tip of needle 132, and thus not cover the tip.

FIG. 12A to 13A show various shapes the safety shield can take. Each shield shown has a concave cavity where the needle tip can be trapped. Each of these shields except 140b show the needle going through the center of the shield. The hole at the center of the shield is indented toward the needle handle. Thus, on the interior of the shield, the hole is upon an apex. This insures the needle cannot accidently slip back through the hole. In FIG. 12A a section view of a safety shield 140a is shown with shaft 50 passing through its center. FIG. 12B shows a variation where a cavity 148 on a shield 140b does not completely encompass shaft 50. FIG. 12C shows a shield 140c with an absorbent pad 152 attached to the front portion of the shield. Pad 152 is used to absorb body fluids that might have collected on shaft 50. As shield 140c slides upward pad 152 absorbs these fluids. In FIG. 13A shield 140d has a funnel shaped absorbent pad 153 attached to the front of the shield.

FIGS. 13A to 13D shows various means of attaching a helical spring to the needle shield. In FIG. 13A a shield 140d is crimped onto the end of a spring 135a with 2 or more crimp tabs 157. These tabs are bent in and around the spring; trapping one or more coils of the spring between tabs 157 and the inside of shield 140d. FIG. 13B shows a shield 140e employing crimp tabs 162 in a fashion similar to shield 140d, but in this design spring 135b fits around the outside of the needle shield. The tabs are then bent out and around the end of the spring. FIG. 13C shows the preferred design with the needle shield crimped radially inward onto the end of spring 135c. The shield and spring can use a spot welded 167 to increase the integrity of the connection. FIG. 13D eliminates the need to bond the spring to the shield by machining the spring directly from the shield. A coil of metal is cut from the base of shield 140g and tempered to give resilience to the metal. Thus, a spring 172 is formed which is an integral part of shield 140g.

OPERATIONAL DESCRIPTION—FIGS. 3a to 3d,

The spring-loaded safety needle is designed to function under the same operating procedures as needles presently used. A safety needle would come inside a pair of sterile protective caps, much like present needles. These caps protect the needle from contamination. When the aft protective cap is removed the receiving hub of the needle is exposed. With the front protective cap covering the sharp portion of the needle the needle can be attached to a syringe without contaminating the needle. For twist-on syringes the front cap communicates rotary motion to the needle. After the needle has been attached the front cap is removed. This exposes the tip of the needle and can now be used to draw blood, give injections, take biopsies, or other medical use. This procedure for using a safety needle is identical to that used with standard needles.

After the safety needle has been used it must be removed from the patient, catheter, or injection port. The practitioner grasps the front of the syringe to remove the needle. However, with a safety needle attached to the syringe, the practitioner also grasps the safety needle's handle which is on the front of the syringe. Their thumb and forefinger resting on the finger grips of the safety needle handle. This leaves their other hand free to place a cotton ball over the puncture sight before removing the needle. After the needle is removed the practitioner squeezes the needle handle. This activates the safety mechanism and the safety shield shoots out to the end of the needle and past the tip. The now stretched spring then rebounds, pulling the shield backward toward the sharp tip of the needle. Because of the manner in which the shield is designed the needle does not come back through the center hole of the shield, but is caught within a circular trough-shaped recession. The impact of the metal shield against the tip of the needle blunts the tip. This effectively destroys the needle tip's ability to easily puncture the skin.

With the safety shield in place over the needle, there is little chance that the needle tip could ever accidently escape. In tests the shield could not be dislodged from the needle by dropping, throwing, or raking it across objects. The spring was responsible for much of this safety because it guides the needle tip back into the concavity and holds it there with spring tension. If the needle tip should be exposed intentionally the risk of accidental puncture is greatly reduced, because the tip has been blunted. Thus, much greater pressure is required to puncture the skin with a damaged tip than with a sharp needle.

Figure 3A:
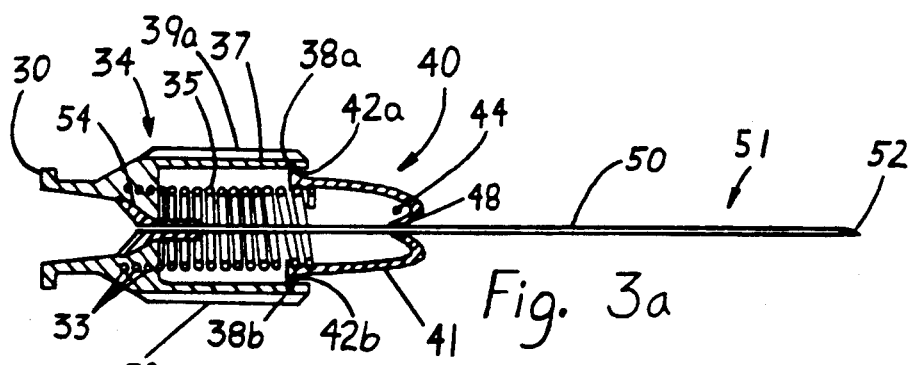
FIG. 3a through 3d shows section views of the 4 states of release for the invention: 4a cocked position; 4b safety shield released and spring in equilibrium; 4c safety shield comes to a momentary stop with spring stretched to maximum length; 4d safety shield pulled down over the tip of the needle with the stretched spring holding it in place.

In FIGS. 3a to 3d the safety needle is shown in its four states of release. FIG. 3a shows the safety needle in its cocked position. Safety shield 40 is held in its retracted position by two flanges 42a and 42b which catch on notches 38a and 38b. After the needle has been used the practitioner presses on finger grips 36a and 36b (see FIG. 2). This causes the finger grip portions of latch tube 37 to move toward the center axis of the invention. At the same time the portions of tube 37 containing latch notches 38a and 38b move away from the center axis. As these notches move out, flanges 42a and 42b slip out of 38a and 38b. The shield is now free to move and spring force accelerates it toward the tip of the needle.

Figure 3B:
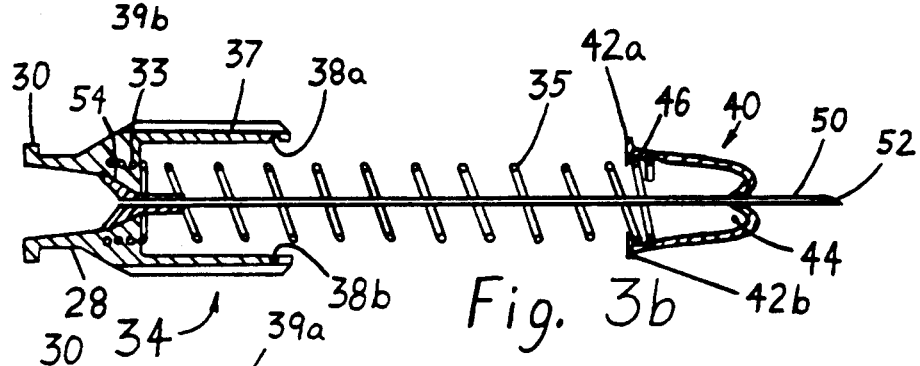

FIG. 3b shows the shield in mid-flight. At some point in its flight the spring will go from being a compression spring to a tension spring. This happens because the momentum of shield 40 carries it past the natural length of the spring.

Figure 3C:
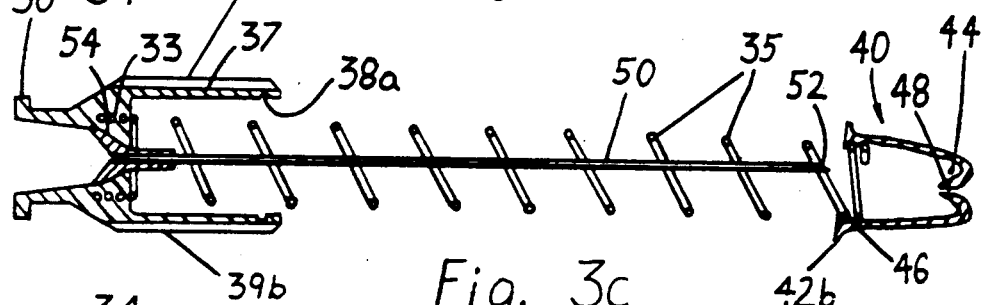

FIG. 3c shows shield 40 at its fully extended position. That is, the momentum of shield 40 has stretched spring 35 to its fully extended position. Shield 40 now accelerates back toward the needle tip. Because shield 40 is now past needle tip 52 there is nothing to keep shield 40 centered and spring forces pull it off center. A slight bend in the spring assures that the shield will not thread needle 50 back through center hole 48. As shield 40 accelerates back toward tip 52 forces may pull the shield too far to the side. If this happens spring 35 acts as a guide, keeping the needle in alignment with the inside of shield 40. Thus, the spring keeps the needle in line with the safety shield even if excess bend causes the needle to slide against the inside of the spring.

Figure 3D:
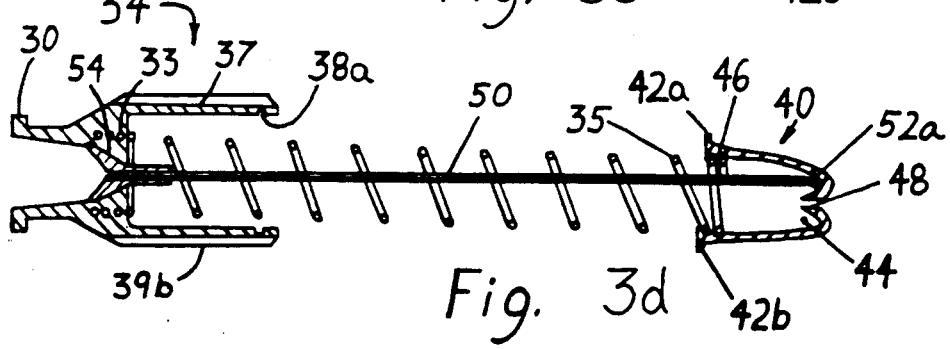

FIG. 3d shows the safety shield in its final resting place. The impact of shield 40 against tip 52 has crushed the end of the needle. Blunted needle tip 52a is sufficiently damaged to make reuse of needle 51 unacceptable because of the forces needed to puncture ones skin and the pain it would cause the user.

OPERATION OF LATCHING SYSTEM FIGS. 4 to 6

In FIG. 4 a section view of the latching system is shown. Notice that this section view cuts through ridge 39a and tube 37. The outside of tube 37 is shown by a dashed line because it is hidden behind ridge 39a. The bevel shown on notch 38a and flange 42a are exaggerated for clarity. This bevel helps insure that an accidental release does not occur. Shield 40 is released when notch 38a is forced away from flange 42a. As soon as flange 42a and 42b (see FIG. 3d) clear flanges 38a and 38b, shield 40 is free to be pushed forward by compressed spring 35.

FIG. 5 shows a representative view of the shape change necessary in tube 37 in order to release shield 40. FIG. 5 can be viewed in conjunction with FIG. 6, where both are views of the safety needle from the front end. That is, the needle pointing toward the reader. In FIG. 5 oval lines 37a and 37b represent two positions tube 37 can possess. Line 37a represents the axial shape of the latch tube before release. When finger grips 36a and 36b are pressed tube 37 deforms and takes on the shape of line 37b. Horizontal arrows 136 represent the motion of grips 36a and 36b when they are pressed. Vertical arrows 142 show the movement of notches 42a and 42b. Notice that as the finger grip portions of the latch tube are pressed together the latch notches are forced apart. As the notches are forced apart the latch flanges are pulled out of the notches and the safety shield is released.

To help stabilize the safety shield notches 38a and 38b do not go completely through tube 37. The back wall of these notches serve two purposes. First, to keep shield 40 from sliding back and forth in the notches. If the ends of flanges 42a and 42b are in contact with the back wall of notches 38a and 38b the shield is effectively trapped. Secondly, because the shield is stabilized by the back walls of the notches the depth of the notches can be reduced and still not risk accidental release. This means that less expansion of tube 37 is needed to release the shield, and thus, tube 37 can be made smaller.

OPERATION OF PROTECTIVE CAPS FIG. 7

FIG. 7 shows front and aft caps 70 and 78 enclosing the safety needle. The caps serve to protect the needle from contamination until it is ready for use. The safety needle would come in a sterile plastic wrapper (not shown) with caps 70 and 78 fitted over safety needle 32. Caps 70 and 78 would be joined together by a small melted section connecting cap 78 to ring 72. To use the safety needle the safety needle with caps on would be removed from its plastic packaging. Aft cap 78 is twisted with respect to cap 70 in order to break the melted section holding them together. Cap 78 is then removed with safety needle 32 snugly fitted in cap 70. Receiving hub 28 is exposed and can now be be twisted onto a syringe nozzle while only gripping cap 70. After the safety needle is connected to a syringe, cap 70 is removed and the needle is ready for use. After use the shield is released to cover the tip as was discussed above.

OPERATION OF OTHER EMBODIMENTS FIGS. 8 to 13

In FIG. 8 a modified embodiment of the invention is shown where the actual safety mechanism is separate from the needle. In this design, a safety mechanism is created that fits over a standard needle. The safety portion of this design is shown in section and a standard needle inside the invention shown in perspective. A standard needle, one which could be found in any hospital in the U.S., is shown comprising of receiving hub 56, ridges 66 on hub 56, base 54, shaft 50, and tip 52. The safety portion of this design operates identically to the design shown in FIGS. 1 to 7. Because many parts are identical I have identified them with the same numbers as in FIGS. 1 through 7.

FIGS. 9 through 13 show different embodiments of the latching system, safety shield design, and spring attachment. FIGS. 9 to 11 show three different embodiments of the latching system and the safety shields that goes with them. FIGS. 12a to 12c and 13a show section views of 4 differently shaped safety shields, and FIGS. 13a to 13d show 4 methods of attaching a safety shield to a spring.

In FIGS. 9a to 9d latching system 82a is combined with a modified safety shield 101. Parts 82a and 101 are arranged in the same configuration as shown in FIG. 8, where shield 101 replaces shield 40 and assembly 82a replaces handle 34A. Assembly 82a can also be molded around a needle as handle 34 is shown molded around needle 51 in FIGS. 1 to 7.

The latching assembly shown in FIG. 9a use rocker arms 91a and 91b to hold shield 101 in a retracted position. Shield 101 is released by pressing one or both rocker handles 92a and 92b.

In FIGS. 9a to 9d, when handles 92a and 92b are pressed, the rocker arms pivot about pivots 94a and 94b. As the rocker arms rotate, catches 96a and 96b are pulled away from shield 101. Immediately upon disengagement of one of the catches from ridge 98, spring pressure pushes that released side of shield 101 outward and away from tube 82a. This sideways motion of shield 101 causes the other catch to disengage and the shield is released. If the catch system is intended to release only if both rocker arms have been pressed then tube lip 95 must be extended past the ends of catches 96a and 96b. With lip 95 extended past catches 96a and 96b shield 101 is not able to rotate to release the second catch. This arrangement requires that ridge 98 has an outside diameter nearly the same as the inside diameter of lip 95. After shield 101 has been released it behaves identically to shield 40 in the preferred embodiment.

FIG. 10 shows latch assembly 82b. This design is used in conjunction with shield 101 shown in FIG. 9c. Ridge 98 on shield 101 when in a retracted position will catch on tabs 86a and 86b (which are exaggerated in size for clarity). Tube 83 is oblong, being flattened along the sides containing ridges 84a and 84b. When tube 83 is pressed in the direction of arrows 85, tabs 86a and 86b are pushed away from each other. As tabs 86a and 86b move away from each other, shield 101 is released.

FIG. 11 shows a complete safety needle with modified latch assembly 82c. In this design, notches 112a and 112b communicate with flanges 124a and 124b to hold shield 130 in a retracted position. Spring 120 is compressed with shield 130 in a retracted position. When finger grips 114a (opposite 114b) and 114b are pressed, tube 110 bends in at these points and notches 112a and 112b move away from each other. This causes shield 130 to release and spring 120 pushes shield 130 to the end of the needle to cover the tip of the needle.

FIGS. 12C and 13A show safety shields which have absorbent pads attached to the front surface of the shield. After a needle is used fluids can collect on the needle's shaft. When a safety shield slides down this 'dirty' shaft fluids can build up on the leading surface. These fluids are then flung off the cap and into the air when the shield makes a quick stop at the needle tip. To prevent this, an absorbent pad is glued, cemented, molded, or by similar means attached to the safety shield. In FIG. 12C pad 152 is in contact with a needle shaft 50. After shield 140c is released fluids on shaft 50 are absorbed into the pad as it slides toward the tip. In FIG. 13A pad 153 works the same way as pad 152 but is designed to have a larger contact surface on the shaft. (It should be noted that if the center hole of the safety shield is enlarged, fluids on the needle shaft could be absorbed by a pad placed on the inside of the shield. However, by making the center hole larger, one increases the chances that the needle tip will escape.)

SUMMARY, RAMIFICATIONS, and SCOPE

Accordingly, the reader should realize that the safety device discussed here can be used to quickly and easily cover needle tips. In addition, the use of this invention blunts the needle tip making reuse of the needle almost impossible for illegal drug users. Furthermore, the spring loaded safety needle has additional advantages in that it provides a compact protective covering system;

it provides a design that is easily incorporated into present medical procedures;

it provides a simple device that is easily manufactured;

it provides a simple latching system that will not accidently release if abused; and it provides a distinctive click when the needle tip is properly protected.

Although the above description of the invention contains many specifications, these should not be viewed as limiting the scope of the invention. Instead, the above description should be considered illustrations of some of the presently preferred embodiments of this invention. For example, the means of extending the safety shield is not limited to helical springs. Modern bent ring mesh springs would work equally well, and having the advantage of being compressible to a very thin cross section. The reason bent ring mesh springs are not used in the preferred embodiment of this invention is because the patent on bent ring mesh springs are still in force and would mean added cost if used, because of royalties. Also, the safety device need not be used only with needles for giving injections or drawing fluids. For example, a cannula insertion needle could have the invention attached to it as could any other similar needle.

Thus the scope of this invention should not be limited to the above examples but should be determined from the following claims.

I claim:

1. A safety device for use in medical procedures using a needle and thereafter providing a covering which destroys the sharp needle tip to protect people form an accidental puncture, comprising:

(a) a needle for use in medical procedures, said needle having at least one sharp tip;

(b) a handle which is molded around one end portion of said needle, with said sharp tip projecting forward, whereby sufficient structural support is provided to said needle for attachment to a syringe;

(c) a shield having a concavity of sufficient size to trap and hold the sharp tip of said needle within said concavity such that friction between said shield and the needle shaft is sufficiently low as to allow unhindered ballistic extention of said shield;

(d) a spring for extending said shield forward along said needle, with said spring substantially connecting said shield to said handle, said spring having an equilibrium length such as to place said shield just below the needle tip, whereby the extension of said shield beyond the needle tip and subsequent covering is achieved by using the momentum of said shield to stretch said spring;

(e) a means for securing said shield to said handle, with said spring compressed between said handle and said shield; and (f) a means for releasing the securing means, whereby said shield can slide forward and past its equilibrium position to cover the needle's tip.

2. The safety device of claim 1, wherein:

said shield defines a center hole for the passage of the needle shaft and where said center hole is indented into said shield such that a circular trough is formed on the interior of said shield with the hole positioned upon an apex created by said indentation with said center hole being of sufficient size so as to provent binding between said shield and the needle shaft, whereby sufficiently low friction is observed to allow covering of the needle tip.

3. The safety device of claim 1, further including:

a plurality of flanges formed on said shield; and said handle defines a cylindrical latch tube, such that a plurality of notches are defined on the interior of said cylindrical latch tube, whereby the flanges communicate with the notches to provide a securing and releasing means for said shield.

4. The safety device of claim 1, wherein:

said handle defines a tubular handle portion with said needle and said spring passing therethrough; whereby radial pressure will cause said tubular handle portion to deform;

said shield defines a plurality of flanges on the outside of said shield, said shield also defining a center hole for the passage of said needle, with said center hole located upon a local apex within the interior of said shield, whereby a circular trough is formed within said shield;

said means for securing said shield to said handle is accomplished by a plurality of notches defined on the interior of said tubular handle portion which communicate with said plurality of flanges; and said means for releasing said securing means is accomplished by deforming said tubular handle portion to increase the spacing between said plurality of notches, whereby said shield can be released by radial pressure exerted on the sides of said tubular handle portion.

5. A safety device for use in conjunction with a standard medical needle and thereafter protecting people from contact with contaminated portions of the needle by blunting the needle tip and also covering the blunted point; said device comprising;

(a) a safety shield having a concavity of sufficient size to trap and hold the sharp tip of said standard medical needle within said concavity, said safety shield being movable between a retracted position and an extended position with sufficiently low interaction friction to allow substantial storage of kinetic energy in said safety shield, whereby extention of the shield beyond its natural length to cover the needle tip is provided by said stored kinetic energy;

(b) a tubular handle member having means associated with one end portion for mounting the base portion of the standard needle with the needle tip extending therethrough, with an opposite end portion having, a means for securing said safety shield to said handle, and a means for release the securing means, whereby radial pressure exerted inwardly on opposite sides of said handle cause release of said safety shield;

(c) a spring for extending the shield forward along the standard needle, with said spring substantially connecting said safety shield to said handle, said spring having a natural length such as to place the shield just below the needle tip, said spring providing sufficient kinetic energy to the shield to extend the shield beyond the tip of the needle, whereby the subsequent crushing impact of the shield against the needle tip produces a distinctive detent which informs the operator the needle is safely protected.

6. The safety device of claim 5, wherein:

said safety shield defines a center hole for the passage of the needle shaft and where said said hole is indented into the shield such that a circular trough is formed on the interior of the shield with the hole positioned upon an apex created by said indentation with said center hole being of sufficient size so as to provent binding between the shield and the needle shaft.

7. The safety device of claim 5, further including:

a plurality of flanges formed on said safety shield; and said handle defines a cylindrical latch tube, such that a plurality of notches are defined on the interior of said cylindrical latch tube, whereby said plurality flanges communicate with said plurality of notches to provide a securing and releasing means for the shield.

* * * * *